(12) United States Patent
Rodgers et al.

(10) Patent No.: US 6,809,109 B2
(45) Date of Patent: Oct. 26, 2004

(54) 2,4-DISUBSTITUTED-PYRIDINE N-OXIDES USEFUL AS HIV REVERSE TRANSCRIPTASE INHIBITORS

(75) Inventors: James D. Rodgers, Landenberg, PA (US); Haisheng Wang, Hockessin, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/603,431

(22) Filed: Jun. 25, 2003

(65) Prior Publication Data

US 2004/0019047 A1 Jan. 29, 2004

Related U.S. Application Data

(60) Provisional application No. 60/392,092, filed on Jun. 27, 2002.

(51) Int. Cl.[7] .................... C07D 401/02; C07D 213/02; A61K 31/44
(52) U.S. Cl. .................... 514/332; 514/272; 514/335; 514/336; 514/352; 546/297; 546/264; 546/269.7; 546/286; 546/288; 546/289; 546/307; 544/333; 544/334; 544/335
(58) Field of Search .................... 514/272, 332, 514/375, 336, 352; 546/264, 269.7, 286, 288, 289, 307, 297; 544/333, 334, 335

(56) References Cited

U.S. PATENT DOCUMENTS

| | | |
|---|---|---|
| 3,470,172 A | 9/1969 | Kaufman |
| 3,495,969 A | 2/1970 | Driscoll |
| 4,839,353 A | 6/1989 | Hosoi et al. |
| 5,001,137 A | 3/1991 | Oe et al. |
| 5,081,133 A | 1/1992 | Schubert et al. |
| 5,202,224 A | 4/1993 | Yamakawa et al. |
| 5,519,021 A | 5/1996 | Young et al. |
| 5,874,430 A | 2/1999 | Christ et al. |
| 6,107,301 A | 8/2000 | Aldrich et al. |
| 6,166,088 A | 12/2000 | Kochanny et al. |
| 6,262,088 B1 | 7/2001 | Phillips et al. |
| 6,384,039 B1 | 5/2002 | Fossa |
| 2001/0000340 A1 | 4/2001 | Chen et al. |

FOREIGN PATENT DOCUMENTS

| | | |
|---|---|---|
| DE | 43 20 347 | 12/1994 |
| EP | 0 476 607 | 9/1991 |
| EP | 0 533 130 | 9/1992 |
| EP | 0 530 994 | 3/1993 |
| EP | 0 735 025 | 3/1996 |
| EP | 1 059 100 | 6/2000 |
| EP | 1 103 553 | 5/2001 |
| GB | 12350 | 4/1971 |
| JP | 7247214 | 9/1995 |
| JP | 2001089452 | 4/2001 |
| WO | WO 93/04047 | 3/1993 |
| WO | WO 95/10506 | 4/1995 |
| WO | WO 95/12583 | 5/1995 |
| WO | WO 95/13273 | 5/1995 |
| WO | WO 95/33750 | 12/1995 |
| WO | WO 96/28427 | 9/1996 |
| WO | WO 98/11094 | 3/1998 |
| WO | WO 98/15547 | 4/1998 |
| WO | WO 99/24404 | 5/1999 |
| WO | WO 00/15635 | 3/2000 |
| WO | WO 00/27825 | 5/2000 |
| WO | WO 01/53263 | 7/2001 |
| WO | WO 01/56990 | 8/2001 |
| WO | WO 01/62233 | 8/2001 |

OTHER PUBLICATIONS

Cossey et al., "Pyridines and Pyridinium Salts from Cyanoacetamides", Aust. J. Chem., vol. 29(5), pp. 1039–1050, 1976.

*Primary Examiner*—Zinna Northington Davis
(74) *Attorney, Agent, or Firm*—Mary K. VanAtten

(57) ABSTRACT

The present invention relates to 2,4-disubstituted pyridine-N-oxide compounds of formula (I):

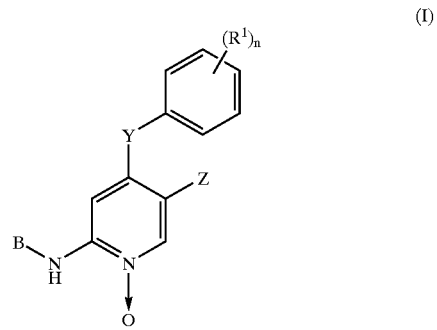

or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

25 Claims, No Drawings

2,4-DISUBSTITUTED-PYRIDINE N-OXIDES USEFUL AS HIV REVERSE TRANSCRIPTASE INHIBITORS

CROSS-REFERENCE TO RELATED APPLICATIONS

The present application claims the priority benefit of U.S. Provisional Application No. 60/392,092, filed Jun. 27, 2002, which is expressly incorporated fully herein by reference.

FIELD OF THE INVENTION

This invention relates generally to pyridine N-oxide compounds and also pyridine N-oxide compounds which are useful as inhibitors of HIV reverse transcriptase, pharmaceutical compositions and diagnostic kits comprising the same, methods of using the same for treating viral infection or as assay standards or reagents, and intermediates and processes for making such pyridine N-oxide compounds.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the consequence of HIV-1 or HIV-2 virus following its complex viral life cycle. The virion life cycle involves the virion attaching itself to the host human T-4 lymphocyte immune cell through the binding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

RNA polymerase transcribes the integrated viral DNA into viral mRNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. In most cases, without therapeutic intervention, HIV causes the host's immune system to be debilitated, allowing opportunistic infections to set in. Without the administration of antiviral agents, immunomodulators, or both, death may result.

There are at least three critical points in the HIV life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treating AIDS. This transcription must occur for the virion to reproduce because the virion's genes are encoded in RNA and the host cell transcribes only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in certain cases in halting HIV replication at the reverse transcriptase (RT) stage.

An active area of research is in the discovery of non-nucleoside HIV reverse transcriptase inhibitors (NNRTIs). As an example, it has been found that certain benzoxazinones and quinazolinones are active in the inhibition of HIV reverse transcriptase, the prevention or treatment of infection by HIV and the treatment of AIDS.

U.S. Pat. No. 5,874,430 describes benzoxazinone non-nucleoside reverse transcriptase inhibitors for the treatment of HIV. U.S. Pat. No. 5,519,021 describe non-nucleoside reverse transcriptase inhibitors which are benzoxazinones of the formula:

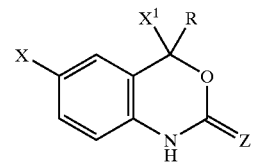

wherein X is a halogen, Z may be O.

EP 0,530,994 and WO 93/04047 describe HIV reverse transcriptase inhibitors which are quinazolinones of the formula (A):

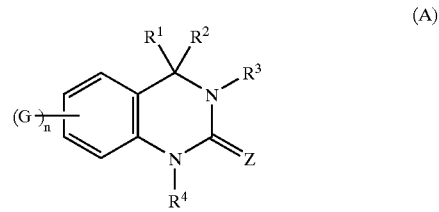

(A)

wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-(−)-6-chloro-4-cyclopropyl-3,4-dihydro-4((2-pyridy)ethynyl)-2(1H)-quinazolinone.

Synthetic procedures for making quinazolinones like those described above are detailed in the following references: Houpis et al., *Tetr. Lett.* 1994, 35(37), 6811–6814; Tucker et al., *J. Med. Chem.* 1994, 37, 2437–2444; and, Huffman et al., *J. Org. Chem.* 1995, 60, 1590–1594.

DE 4,320,347 illustrates quinazolinones of the formula:

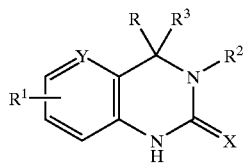

wherein R is a phenyl, carbocyclic ring, or a heterocyclic ring. Compounds of this sort are not considered to be part of the present invention.

Even with the current success of reverse transcriptase inhibitors, it has been found that HIV patients can become resistant to a given inhibitor. Thus, there is an important need to develop additional inhibitors to further combat HIV infection.

SUMMARY OF THE INVENTION

Accordingly, the present invention provides novel reverse transcriptase inhibitors.

The present invention provides novel 2,4-disubstituted pyridine N-oxide compounds.

The present invention provides novel methods for treating HIV infection which comprises administering to a host in need of such treatment a therapeutically effective amount of the compound of the present invention, including a pharmaceutically acceptable salt form thereof.

The present invention provides novel methods for treating HIV infection which comprises administering to a host in need thereof a therapeutically effective combination of (a) at least one of the compounds of the present invention and (b) one or more compounds selected from the group consisting of HIV reverse transcriptase inhibitors and HIV protease inhibitors.

The present invention provides pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

The present invention provides novel 2,4-disubstituted pyridine N-oxide compounds for use in therapy.

The present invention provides the use of novel 2,4-disubstituted pyridine N-oxide compounds for the manufacture of a medicament for the treatment of HIV infection.

These and other aspects, which will become apparent during the following detailed description, have been achieved by the inventors' discovery that compounds of formula (I):

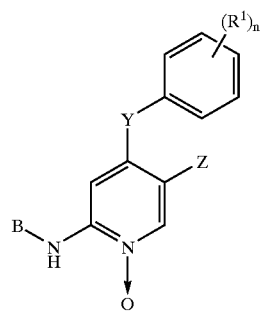

including any stereoisomeric form, mixtures of stereoisomeric forms, complexes, prodrug forms or pharmaceutically acceptable salt forms thereof, wherein B, Y, Z, n and $R^1$ are defined below, are effective reverse transcriptase inhibitors.

DETAILED DESCRIPTION OF EMBODIMENTS OF THE INVENTION

[1] Thus, in a first embodiment, the present invention provides a novel compound of formula (I):

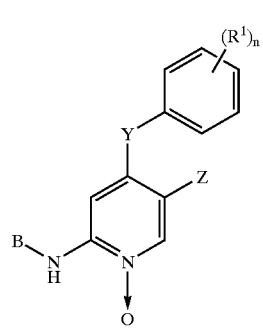

or a stereoisomeric form or mixture of stereoisomeric forms or a pharmaceutically acceptable salt form thereof, wherein B is selected from phenyl substituted with 1–3 X, and a 5–6 membered heterocyclic system containing 1–4 heteroatoms selected from N, O, and S, substituted with 1–3 X;

$R^1$, at each occurrence, is individually selected from F, Cl, Br, I, CN, and $C_{1-4}$ alkyl, $C_{1-3}$ alkoxy n is selected from 1, 2, 3 and 4;

X is selected from CN, F, Cl, Br, and I;

Y is selected from —$CH_2$—, —NH—, and —O—; and

Z is selected from F, Cl, Br, CN, and $C_{1-4}$ alkyl.

[2] In another embodiment the present invention provides novel compounds of formula (I-i), wherein:

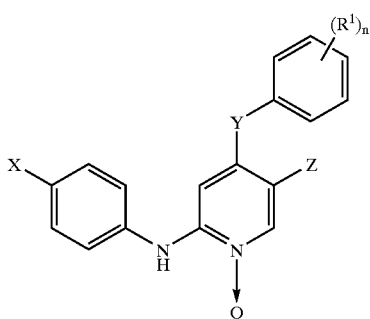

(I-i)

or a stereoisomeric form or mixture of stereoisomeric forms or a pharmaceutically acceptable salt form thereof, wherein
$R^1$, at each occurrence, is individually selected from F, Cl, Br, I, CN, and $C_{1-4}$ alkyl, $C_{1-3}$ alkoxy
n is selected from 1, 2, 3 and 4;
X is selected from CN, F, Cl, Br, and I;
Y is selected from —$CH_2$—, —NH—, and —O—; and
Z is selected from F, Cl, Br, CN, and $C_{1-4}$ alkyl.

[3] In another embodiment the present invention provides novel compounds of formula (I-ii), wherein:

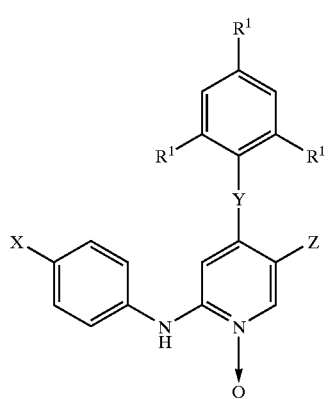

(I-ii)

or a stereoisomeric form or mixture of stereoisomeric forms or a pharmaceutically acceptable salt form thereof.

[4] In another embodiment the present invention provides novel compounds of formula (I), (I-i), or (I-ii), wherein:
$R^1$, at each occurrence, is individually selected from CN, F, Cl, Br, methyl, ethyl, and propyl, i-propyl, methoxy, ethoxy, propoxy, i-propxoy.

[5] In another embodiment the present invention provides novel compounds of formula (I), (I-i), or (I-ii), wherein:
X is selected from F, Cl, Br, and CN.

[6] In another embodiment the present invention provides novel compounds of formula (I), (I-i), or (I-ii), wherein:
Z is selected from Z is selected from Cl, Br, CN, methyl, ethyl and propyl.

[7] In another embodiment the present invention provides novel compounds of formula (I), (I-i), or (I-ii), wherein:
Y is —$CH_2$—.

[8] In another embodiment the present invention provides novel compounds of formula (I), (I-i), or (I-ii) wherein:
Y is —NH—.

[9] In another embodiment the present invention provides novel compounds of formula (I), (I-i), or (I-ii), wherein:
Y is —O—.

[10] In another embodiment the present invention provides novel compounds of formula (I), wherein:
B is selected from phenyl substituted with 1–3 X, and a 5–6 membered heterocyclic system containing 1–4 heteroatoms selected from N, O, and S, substituted with 1–3 X, wherein the heterocyclic system is selected from pyridine, pyrimidine, and thiazole.

[10] In another embodiment the present invention provides novel compounds of formula (I), wherein the compound is selected from:
5-bromo-2-(4-chloroanilino)-4-(2,4,6-trimethylphenoxy) pyridine-N-oxide;
5-bromo-2-(4-chloroanilino)-4-(2,4,6-trimethylanilino) pyridine-N-oxide;
6-[5-Bromo-4-(4-cyano-2,6-dimethyl-phenoxy)-1-oxy-pyridin-2-ylamino]-nicotinonitrile;
[5-Bromo-4-(4-bromo-2,6-dimethyl-phenoxy)-1-oxy-pyridin-2-yl]-(5-bromo-pyridin-2-yl)-amine; and
[5-Bromo-4-(4-Cyano-2,6-dimethyl-phenoxy)-1-oxy-pyridin-2-yl]-(4-cyano-phenyl)-amine.

The present invention also provides a novel pharmaceutical composition comprising a pharmaceutically acceptable carrier and a therapeutically effective amount of a compound of formula (I) or a pharmaceutically acceptable salt form thereof The compositions and methods of use comprising the compounds of the present invention include compositions and methods of use comprising the compounds of the present invention and stereoisomeric forms thereof, mixtures of stereoisomeric forms thereof, complexes thereof, crystalline forms thereof, prodrug forms thereof and pharmaceutically acceptable salt forms thereof.

In another embodiment, the present invention provides a novel method for treating HIV infection which comprises administering to a host in need of such treatment a therapeutically effective amount of a compound of formula (I) or a pharmaceutically acceptable salt form thereof.

In another embodiment, the present invention provides a novel method of treating HIV infection which comprises administering, in combination, to a host in need thereof a therapeutically effective amount of:
(a) a compound of formula (I); and
(b) at least one compound selected from the group consisting of HIV reverse transcriptase inhibitors and HIV protease inhibitors.

In another embodiment, the present invention provides a novel method of treating HIV infection which comprises administering, in combination, to a host in need thereof a therapeutically effective amount of:
(a) a compound of formula (I); and
(b) at least one compound selected from the group consisting of HIV reverse transcriptase inhibitors, HIV protease inhibitors, CCR-5 inhibitors, and fusion inhibitors.

Reverse transcriptase inhibitors useful in the above method of treating HIV infection are selected from the group AZT, ddC, ddI, d4T, 3TC, delavirdine, efavirenz, nevirapine, trovirdine, MKC-442, HBY 097, HBY1293, GW867, ACT, UC-781, UC-782, RD4-2025, MEN 10979, AG1549 (S1153), TMC-120, TMC-125, Calanolide A, and PMPA. Protease inhibitors useful in the above method of treating HIV infection are selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, ABT-378, DMP-450, AG-1776, VX-175, MK-944, and VX-478. The CCR-5 inhibitor is selected from TAK-779 (Takeda), SC-351125 (SCH-C, Schering) and SCH-D (Schering), and the fusion inhibitor is selected from T-20 and T1249.

In another embodiment, the reverse transcriptase inhibitor is selected from the group AZT, efavirenz, and 3TC and the protease inhibitor is selected from the group saquinavir, ritonavir, nelfinavir, and indinavir.

In another embodiment, the reverse transcriptase inhibitor is AZT.

In another embodiment, the protease inhibitor is indinavir.

In another embodiment, the present invention provides a pharmaceutical kit useful for the treatment of HIV infection, which comprises a therapeutically effective amount of:
  (a) a compound of formula (I); and,
  (b) at least one compound selected from the group consisting of HIV reverse transcriptase inhibitors and HIV protease inhibitors, in one or more sterile containers.

In another embodiment, the present invention provides novel pyridine N-oxide compounds for use in therapy.

In another embodiment, the present invention provides the use of novel pyridine N-oxide compounds for the manufacture of a medicament for the treatment of HIV infection.

In another embodiment, the present invention provides a compound of formula (I), wherein B is a 5–6 membered heterocyclic system containing 1–4 heteroatoms selected from N, O, and S, substituted with 1–3 X, wherein the heterocyclic system is selected from pyridine, pyrimidine, and thiazole.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "substituted," as used herein, means that any one or more hydrogens on the designated atom or ring is replaced with a selection from the indicated group, provided that the designated atom's normal valency is not exceeded, and that the substitution results in a stable compound. When a substitent is keto (i.e., =O), then 2 hydrogens on the atom are replaced.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, the following terms and expressions have the indicated meanings.

When any variable (e.g., $R^1$) occurs more than one time in any constituent or formula for a compound, its definition at each occurrence is independent of its definition at every other occurrence. Thus, for example, if a group is shown to be substituted with 0–2 $R^1$, then said group may optionally be substituted with up to two $R^a$ groups and $R^a$ at each occurrence is selected independently from the definition of $R^1$. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. By way of illustration, the term "$C_{1-10}$ alkyl" or "$C_1$–$C_{10}$ alkyl" is intended to include $C_1$, $C_2$, $C_3$, $C_4$, $C_5$, $C_6$, $C_7$, $C_8$, $C_9$, and $C_{10}$ alkyl groups. "$C_{1-4}$ alkyl" is intended to include $C_1$, $C_2$, $C_3$, and $C_4$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example –$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" is intended to include hydrocarbon chains of either a straight or branched configuration and one or more unsaturated carbon-carbon bonds which may occur in any stable point along the chain, such as ethenyl, propenyl and the like. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon-carbon bonds which may occur in any stable point along the chain, such as ethynyl, propynyl and the like. $C_{2-10}$ alkynyl, is intended to include $C_2$, $C_3$, $C_4$, $C_5$, $C_6$, $C_7$, $C_8$, $C_9$, and $C_{10}$ alkynyl groups.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7- membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), efavirenz (BMS), nevirapine (Boehringer Ingelheim), Ro 18,893 (Roche), trovirdine (Lilly), MKC-442 (Triangle), HBY 097 (Hoechst), HBY1293 (Hoechst), GW867 (Glaxo Wellcome), ACT (Korean Research Institute), UC-781 (Rega Institute), UC-782 (Rega Institute), RD4-2025 (Tosoh Co. Ltd.), MEN 10979 (Menarini Farmaceutici) and AG1549 (S1153; Agouron) ), TMC-120, TMC-125, and Calanolide A.

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), tipranavir (Pharmacia and Upjohn, U-140690), DMP-450 (DuPont), AG-1776, VX-175, MK-944, VX-478 and ABT-378. Additional examples include the cyclic protease inhibitors disclosed in WO93/07128, WO 94/19329, WO 94/22840, and WO96/29329.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Further examples of prodrugs at are $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Therapeutically effective amount" is intended to include an amount of a compound of the present invention alone or in combination with other active ingredients or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

The compounds of the present invention, wherein Y is a carbon atom, maybe prepared using the procedure shown in Scheme 1. Condensation of 4-pyridine carboxaldehyde with mesityl lithium afforded alcohol 2. Reduction of 2 with triethylsilane in TFA gave pyridine 3. Oxidation of 3 with MCPBA followed by rearrangement of the N-oxide with $POCl_3$ yielded the 2-chloropyridine 4. Condensation of 4 with 4-chloroaniline gave pyridine 5. After protection of the central nitrogen as the carbamate, the pyridine ring was brominated with NBS, oxidized with MCPBA and finally deprotected with TFA to afford the target compound 6. While the procedure shown in Scheme 1 is shown to specific substituents, the procedure may also be used to prepare the compounds of the present invention having many other substituents. Furthermore, the procedure may be used to prepare compounds wherein B is equal to a heterocyclic residue or a substituted heterocyclic residue.

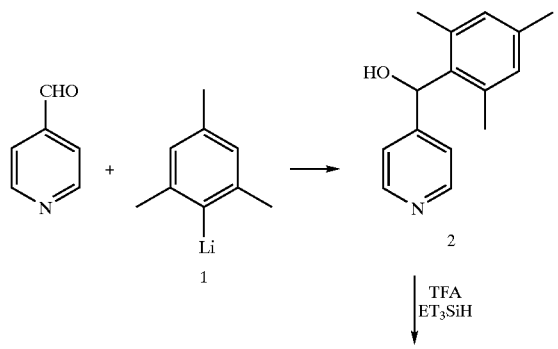

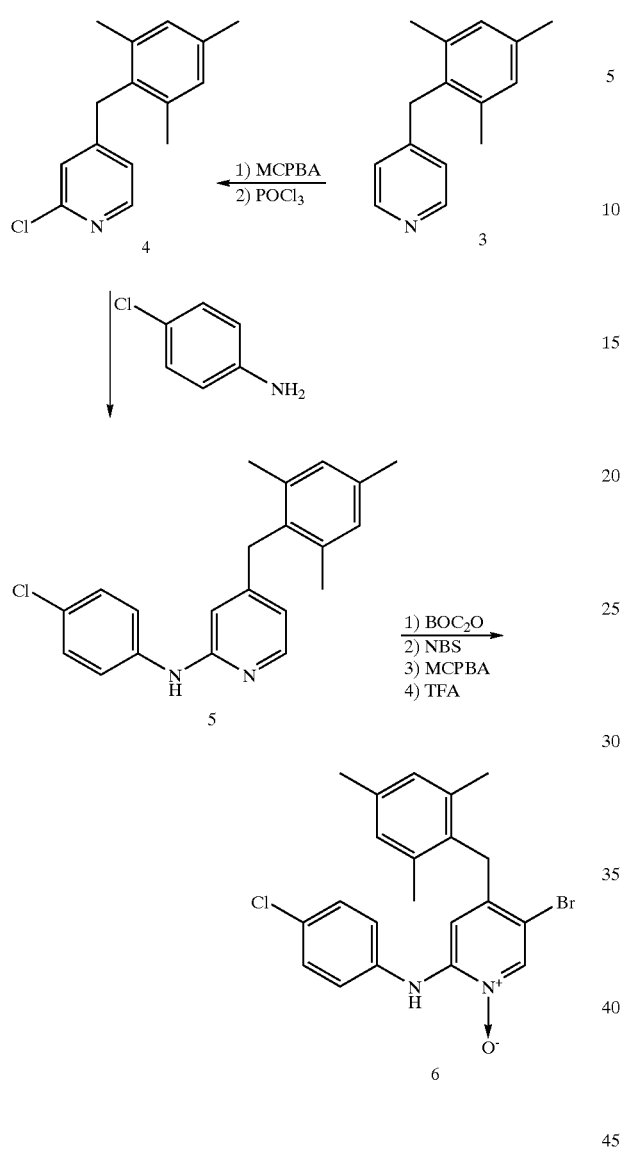

The compounds of the present invention, wherein Y is N or O, can be prepared as described in the attached examples. Both series of compounds have a key intermediate A (i.e. compound 2 in example 1, compound 8 in example 2). When X=NH, an aniline reacts with 2,4-dichloropyridine neat; When X=O, a preformed phenoxide reacts with 4-chloropyridine-N-oxide neat or in a solvent (DMF, NMP), the resulting N-oxide is rearranged to the 2-chloropyridine; When X=CH$_2$, an appropriate benzyl anion (generated by PhLi or LDA) reacts with 4-chloropyridine-N-oxide in THF, the resulting N-oxide is rearranged to the 2-chloropyridine.

Compound A is coupled with the appropriately substituted aniline, then Boc-protected, bromonated, deprotected and oxidized to the final products. Alternatively, compound A may be coupled with an appropriately substituted aminoheterocycle to give compounds wherein B is a heterocyclic residue.

EXAMPLES

All reactions were run under a nitrogen atmosphere and most were unoptimized. The reactions were followed by TLC. Reagents were used as received. DMF, THF and NMP were dried over molecular sieves, All other solvents were reagent grade. 2,4-Dichloropyridine was prepared by refluxing 2,4-dihydroxypyridine with POCl$_3$. Column chromatographies were done on flash silica gel.

Example 1

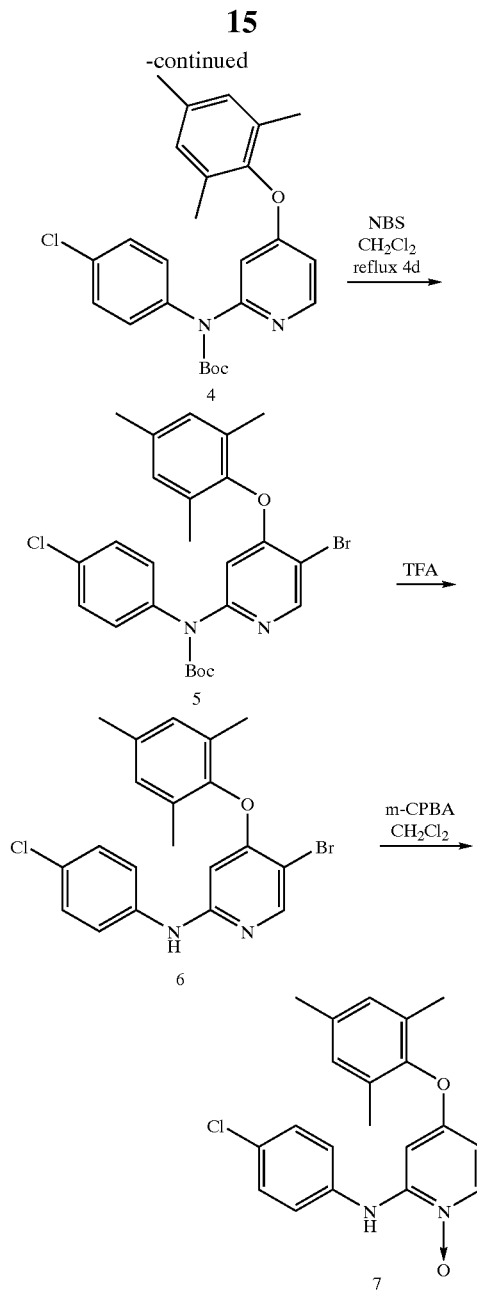

washed with water, 0.1N HCl, water and saturated NaCl. The organic phase was dried over Na₂SO₄ and evaporated. Crystallization and chromatography (25% EtOAc/hexanes) gave a pale pink solid (3, 690 mg, 78% yield).

Step D: A suspension of 3 (455 mg, 1.34 mmol), pyridine (217 μL), (Boc)₂O (500 mg, 2.29 mmol), DMAP (29 mg) in CH₂Cl₂ (5 mL) became a solution after stirred for 0.5 h and continued to stir for 2 h. The reaction was diluted with EtOAc, washed with 1N HCl (3×), 1NaOH and saturated NaCl (2×). The organic phase was dried over Na₂SO₄ and evaporated to give pale pink oil (4, 700 mg).

Step E: A solution of 4 (600 mg, 1.34 mmol) and NBS (239 mg, 1.34 mmol) in CH₂Cl₂ (9 mL) was refluxed for 4 days. The reaction was diluted with EtOAc, washed with 1N NaOH (2×)and saturated NaCl. The organic phase was dried over Na₂SO₄ and evaporated to give orange oil Chromatography (15% EtOAc/hexanes) and crystallization gave an orange oil (5, 207 mg).

Step F: A solution of (5, 207 mg) in TFA (0.3 mL) and CH₂Cl₂ (3 mL) was stirred overnight. The solvents were evaporated and the oil was diluted with EtOAc, washed with 1N NaOH (2×) and saturated NaCl. The organic phase was dried over Na₂SO₄ and evaporated to give a brown solid (6, 172 mg). A solution of 6 (162 mg) and m-CPBA (173 mg) in CH₂Cl₂ (5 mL) was stirred over weekend and Me₂S was added. The solvent was evaporated and the oil was diluted with EtOAc, washed with 1N NaOH (2×) and saturated NaCl. The organic phase was dried over Na₂SO₄ and evaporated to give a brown solid, which was triturated with ether to give a brown solid (54 mg). The solid was crystallized from dichloroethane to give an off-white solid (7, 15 mg): mp 249–250° C.; MS 422 (M+H)

Example 2

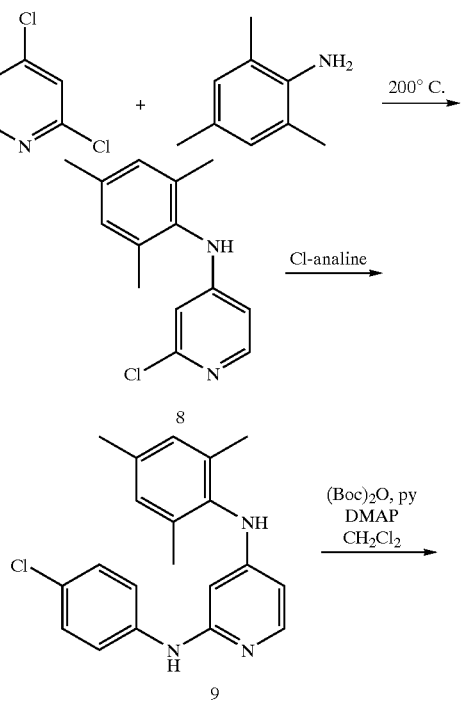

Synthesis of 5-bromo-2-(4-chloroanilino)-4-(2,4,6-trimethylphenoxy)pyridine-N-oxide (7)

Step A: A mixture of 2,4,6-trimethylphenol (3.15 g, 23.2 mmol) and NaH (0.31 g, 7.7 mmol) was heated at 100 °0 for 20 min., then 4-chloro-pyridine-N-oxide was added and the mixture was heated at 120 ° 0 for 4 h. The reaction was diluted with EtOAc, washed with water (3×) and saturated NaCl (2×). The organic phase was dried over Na₂SO₄ and evaporated to give black oil. Chromatography (5% MeOH/CH₂Cl₂) gave an orange oil (1, 1.51 g, 85% yield).

Step B: A solution of 1 (1.5 g) in POCl₃ (15mL) was refluxed overnight. The solvent was evaporated and the oil was diluted with EtOAc, washed with 1N NaOH and saturated NaCl. The organic phase was dried over Na₂SO₄ and evaporated to give orange oil. Chromatography (10→15% EtOAc/hexanes) gave an orange oil (2, 0.93 g, 62% yield).

Step C: A mixture of 2 (623 mg, 2.51 mmol) and 4-chloroaniline (639 mg, 5.01 mmol) was heated at 120° C. for 5 h. The reaction was diluted with EtOAc and THF,

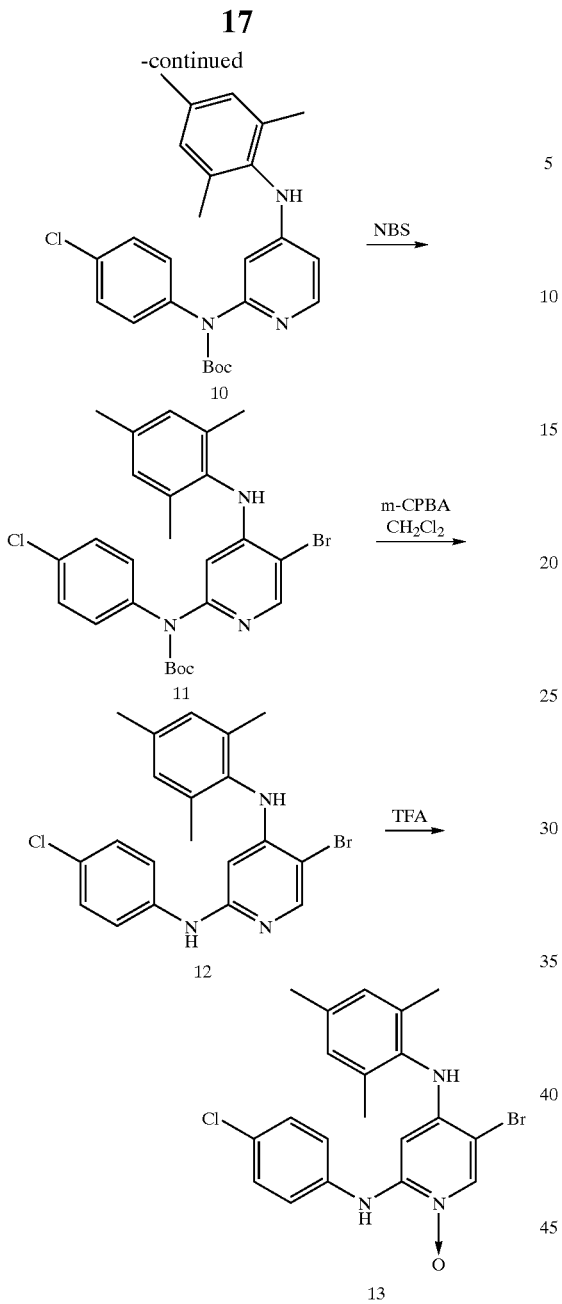

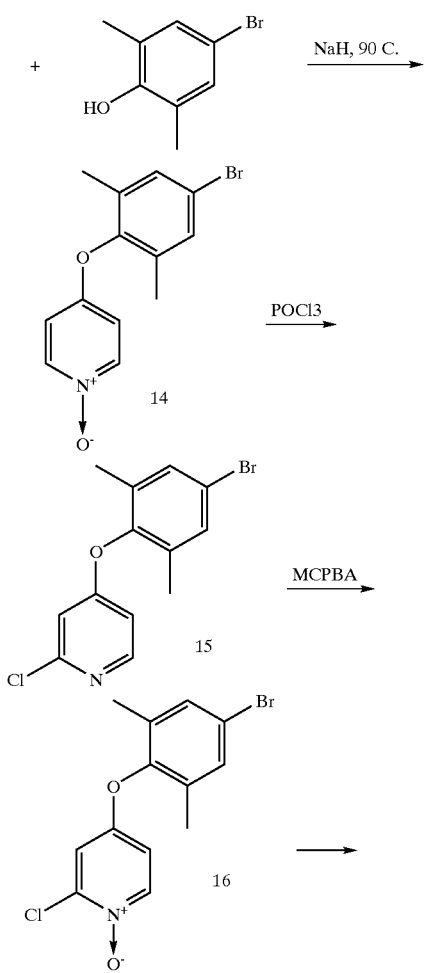

NaCl (2×). The organic phase was dried over $Na_2SO_4$ and evaporated Chromatography (25% EtOAc/hexanes) gave an oil (10, 130 mg).

Step D: A solution of 10 (130 mg, 0.3 mmol) and NBS (53 mg, 0.3 mmol) in $CH_2Cl_2$ (2 mL) was stirred at −78° C. for 15 min. The reaction was diluted with EtOAc, washed with 1N NaOH (2×) and saturated NaCl. The organic phase was dried over $Na_2SO_4$ and evaporated to give a glass. Chromatography (10% EtOAc/hexanes) gave an oil (11, 71 mg).

Step E: A solution of 11 (71 mg) and m-CPBA (123 mg) in $CH_2Cl_2$ (4 mL) was stirred over weekend and $Me_2S$ was added. The solvent was evaporated and the oil was diluted with EtOAc, washed with 1N NaOH (2×) and saturated NaCl. The organic phase was dried over $Na_2SO_4$ and evaporated to give orange oil. Chromatography (2.5→5% MeOH/$CH_2Cl_2$) gave an oil (12, 15 mg).

A solution of (12, 15 mg) in TFA (0.2 mL) and $CH_2Cl_2$ (2 mL) was stirred overnight. The solvents were evaporated and the oil was diluted with EtOAc, washed with 1N NaOH (2×) and saturated NaCl. The organic phase was dried over $Na_2SO_4$ and evaporated to give an off-white solid, which was triturated with ether to give a white solid (13, 5 mg): mp 235–237° C.; MS 433 (M+H).

Example 3

Synthesis of 5-bromo-2-(4-chloroanilino)-4-(2,4,6-trimethylanilino)pyridine-N-oxide (13)

Step A: A mixture of 2,4-dichloropyridine (570 mg, 3.63 mmol) was heated at 200 °0 for 5 h. EtOAc and saturated $NaHCO_3$ were added and insoluble solid was filtered off. The filtrate was washed with saturated $NaHCO_3$ and saturated NaCl. Chromatography (25% EtOAc/hexanes) gave an orange oil (8, 210 mg).

Step B: A mixture of 8 (200 mg, 0.81 mmol) and 4-chloroaniline (206 mg, 1.62 mmol) was heated at 185° C. overnight. The reaction was diluted with EtOAc and was washed with saturated $NaHCO_3$ and saturated NaCl. Chromatography (5% MeOH/$CH_2Cl_2$) gave brown solid (9, 208 mg).

Step C: A suspension of 9 (180 mg, 0.53 mmol), pyridine (86 μL), $(Boc)_2O$ (390 mg, 1.8 mmol), DMAP (15 mg) in $CH_2Cl_2$ (2 mL) became a solution after stirred for 5 min. and continued to stir for 15 min. The reaction was diluted with EtOAc, washed with 1N HCl (2×), 1NaOH and saturated

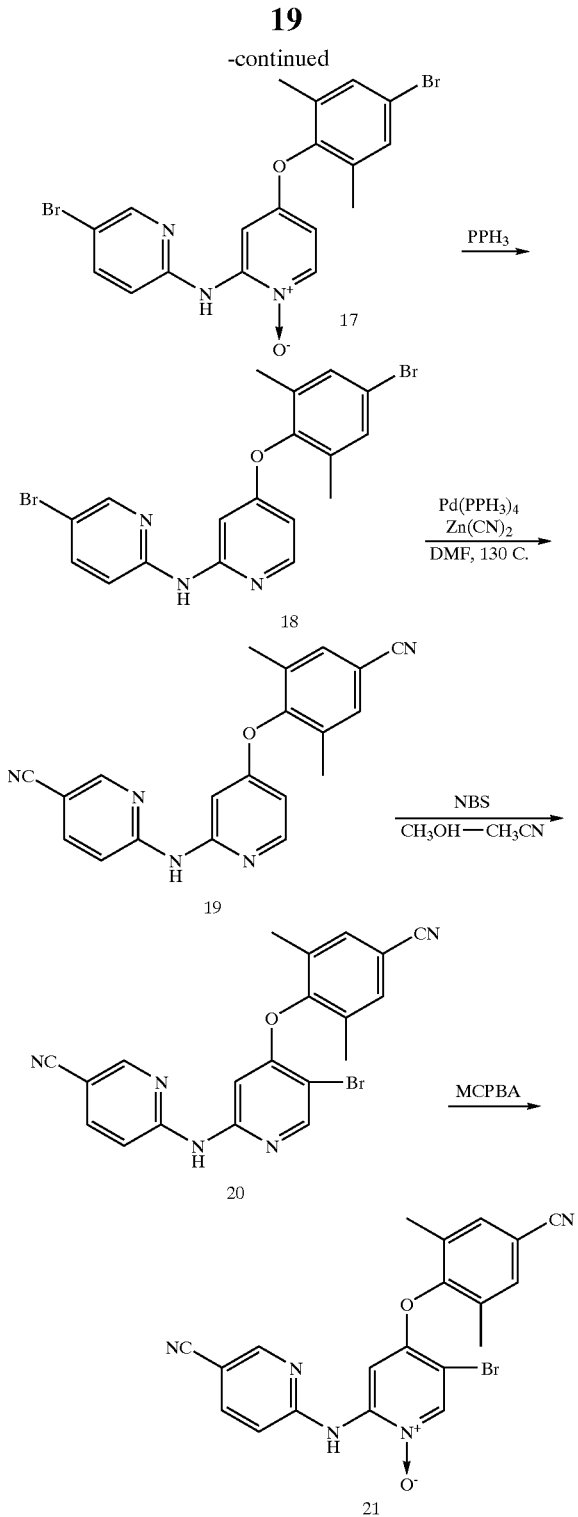

added and the reaction was heated to 90° C. overnight. After cooling to RT, the mixture was partitioned between EtOAc (1L) and 1N NaOH soln (500 mL). The organic phase was washed with 1N NaOH solution (2X), $H_2O$ (1X), brine and dried over $MgSO_4$. Column chromatography ($SiO_2$, 90 mm×18 cm, 5–10% $CH_3OH$—$CH_2Cl_2$, 2% $Et_3N$) afforded the desired material as a brown solid (20.66 g, 61%). $^1H$ NMR (300 MHz, $CDCl_3$) δ8.11 (dd, J=1.8, 5.5 Hz, 2 H), 7.28 (s, 2H), 6.70 (dd, J=2.2, 5.5 Hz, 2H), 2.10 (s, 6H). ESI-MS m/z 294.2 ($M^+$+H)

Step B: 4-(4-Bromo-2,6-dimethyl-phenoxy)-2-chloro-pyridine (15): A suspension of 4-(4-Bromo-2,6-dimethyl-phenoxy)-pyridine 1-oxide (14, 10 g, 34 mmol, 1 equiv) and $Na_2CO_3$ (3.6 g, 34 mmol, 1 equiv) in $POCl_3$ (100 mL) was heated to 105° C. for 30 h. The reaction was cooled to RT and the $POCl_3$ was removed by rotary evaporation. The residue was dissolved in EtOAc and partioned into a chilled biphasic solution of EtOAc and 1 N NaOH. The aqueous layer was treated with NaOH (s) until the pH >1. The aqueous layer was extracted with EtOAc (3×), and the combined organics were washed with brine, dried ($MgSO_4$) and concentrated. Recrystallization (EtOH) provided the desired material as off-white crystals (73%). $^1H$ NMR (300 MHz, $CDCl_3$) δ8.21 (d, J=6.2 Hz, 1H), 7.28 (s, 2H), 6.66 (m, 2H), 2.10 (s, 6H). $^{13}C$ NMR (100 MHz, $CDCl_3$) δ165.6, 153.5, 151.3, 149.0, 133.3, 132.5, 119.6, 110.7, 110.2, 16.4.

Step C: 4-(4-Bromo-2,6-dimethyl-phenoxy)-2-chloro-pyridine 1-oxide (16): A solution of 4-(4-Bromo-2,6-dimethyl-phenoxy)-2-chloro-pyridine (100 mg, 0.32 mmol) dissolved in $CH_2Cl_2$ and treated with MCPBA (68.7%, 96 mg, 0.38 mmol, 1.2 equiv). The reaction mixture was stirred at RT overnight. 5 drops of dimethyl sulfide was added and the reaction mixture was concentrated. The resulting yellow solid was triturated with $Et_2O$ to provide 74 mg (70%) of an off-white solid. NMR shows desired material contaminated with a small amount of 15. $^1H$ NMR (300 MHz, $CDCl_3$) δ8.24 (d, J=7.3 Hz, 1H), 7.30 (s, 2H), 6.88 (d, J=3.3 Hz, 1H), 6.69 (dd, J=3.3, 7.3 Hz, 1H) 2.10 (s, 6H).

Step D: [4-(4-Bromo-2,6-dimethyl-phenoxy)-1-oxy-pyridin-2-yl]-(5-bromo-pyridin-2-yl)-amine (17): A solution of 2-amino-5-bromopyridine (79 mg, 0.456 mmol, 3 equiv) in THF at 0° C. was treated with NaHMDS (1.0 M in THF, 500 μL, 0.5 mmol, 3.3 equiv) and stirred for 30 minutes. 4-(4-Bromo-2,6-dimethyl-phenoxy)-2-chloro-pyridine 1-oxide (16, 50 mg, 0.152 mmol, 1 equiv) was added and the reaction was stirred at 0° C. After 2 h, the mixture was partitioned between EtOAc and $H_2O$. The organic layer was washed with 0.1 N HCl, brine and concentrated to an orange glass. Trituration with warm $Et_2O$ (3 mL) containing 3 drops of $CH_2Cl_2$ provided the desired product as a brown solid (51 mg, 72%). Mp 230–5° C. $^1H$ NMR (300 MHz, $CDCl_3$) δ9.77 (brs , NH), 8.30 (d, J=3.3 Hz, 1H), 8.27 (d, J=1.9 Hz, 1H), 8.10 (d, J=7.4 Hz, 1H), 7.72 (dd, J=2.3, 8.8 Hz, 1 H) 7.30 (s, 2H), 6.88 (d, J=8.8 Hz, 1H), 6.22 (dd, J=3.3, 7.4 Hz, 1H), 2.10 (s, 6H).

Step E: [4-(4-Bromo-2,6-dimethyl-phenoxy)-pyridin-2-yl]-(5-bromo-pyridin-2-yl)-amine (18): A mixture of [4-(4-Bromo-2,6-dimethyl-phenoxy)-1-oxy-pyridin-2-yl]-(5-bromo-pyridin-2-yl)-amine (17, 217 mg, 0.467 mmol) was dissolved in DMF (4 mL) and treated with $Ph_3P$-polymer (760 mg). The mixture was heated to reflux for overnight. After filtering the beads were washed with DMF (4×4 mL). The combined filtrate was diluted with EtOAc and washed with $H_2O$ (2X), brine and dried. Column chromatography ($SiO_2$, 25% EtOAc-hexane) provided the desired material as a pale yellow glass (165 mg, 79%). $^1H$ NMR (300 MHz, $CDCl_3$) δ8.70 (br s , NH), 8.21 (d, J=2.2 Hz, 1H) 7.99 (d, Synthesis of 6-[5-Bromo-4-(4-cyano-2,6-dimethyl-phenoxy)-1-oxy-Pyridin-2-ylamino]-nicotinonitrile (21)

Step A: 4-(4-Bromo-2,6-dim thyl-phenoxy)-pyridine 1-oxide (14): A solution of 4-bromo-2,6-dimethylphenol (46.6 g, 232 mmol, 2 equiv) in NMP (n-methylpyrrolidinone) (75 mL) was treated with six portions of NaH (60%, 9.26 g, 232 mmol, 2 equiv). The resulting mixture was stirred at 23° C. for 2 h then heated to 100° C. for 45 min. The reaction was cooled, 4-chloropyridine N-oxide (15 g, 116 mmol, 1 equiv) was J=5.9 Hz, 1H), 7.63 (dd, J=2.2, 8.8 Hz, 1H), 7.47 (d, J=8.8 Hz, 1H), 7.24 (s, 2H), 6.99 (d, J=1.8 Hz, 1H), 6.29 (dd, J=1.8, 5.9 Hz, 1H), 2.10 (s, 6H).

Step F: 6-[4-(4-Cyano-2,6-dimethyl-phenoxy)-pyridin-2-ylamino]-nicotinonitrile (19): A suspension of 18 (165 mg, 0.367 mmol), zinc cyanide (60 mg, 0.514 mmol, 1.4 equiv), and tetrakistriphenylphosphine palladium (0) (42 mg, 0.37 mmol, 0.1 equiv) in DMF was heated to 130° C. for 9.5 h. Column chromatography (SiO$_2$, 25–35% EtOAc-hexane) afforded the product as a white solid (98 mg, 78%).

Step G: 6-[5-Bromo-4-(4-cyano-2,6-dim thyl-phenoxy)-pyridin-2-ylamino]-nicotinonitrile (20): A suspension of 19 (98 mg, 0.287 mmol) and NBS (56 mg, 0.316 mmol, 1.1 equiv) in CH$_3$CN:CH$_3$OH (10:1, 3 mL) was stirred at room temperature overnight. The precipitated product was filtered and washed to afford the desired product as a white solid (88 mg, 73%). $^1$H NMR (300 MHz, CDCl$_3$) δ8.37 (s, 1H), 8.31 (d, J=1.9 Hz, 1H), 7.79 (dd, J=2.2, 8.8 Hz, 1H), 7.56 (d, J=8.8 Hz, 1H), 7.51 (s, 2H), 6.73 (s, 1H), 2.21 (s, 6H).

Step H: 6-[5-Bromo-4-(4-cyano-2,6-dimethyl-phenoxy)-1-oxy-pyridin-2-ylamino]-nicotinonitrile (21): A solution of 20 (86 mg, 0.204 mmol) in CDCl$_3$ (2 mL) at 0° C. in CDCl$_3$ (2 mL) was treated with MCPBA (51 mg, 0.204 mmol, 1 equiv). NMR showed a 3:2 mixture of desired:undesired mono-N-oxide. Column chromatography (2.5% CH$_3$OH—CH$_2$Cl$_2$) provided the desired product as a white solid (35 mg, 39%). mp 280° C. (decomp) $^1$H NMR (300 MHz, CDCl$_3$) δ8.51 (s, 1H), 8.21 (d, J=1.5 Hz, 1H), 7.99 (s, 1H), 7.82 (d, J=2.2, 8.8 Hz, 1 H) 7.53 (s, 1H), 7.09 (d, J=8.8 Hz, 1H), 2.21 (s, 6H).

Example 4

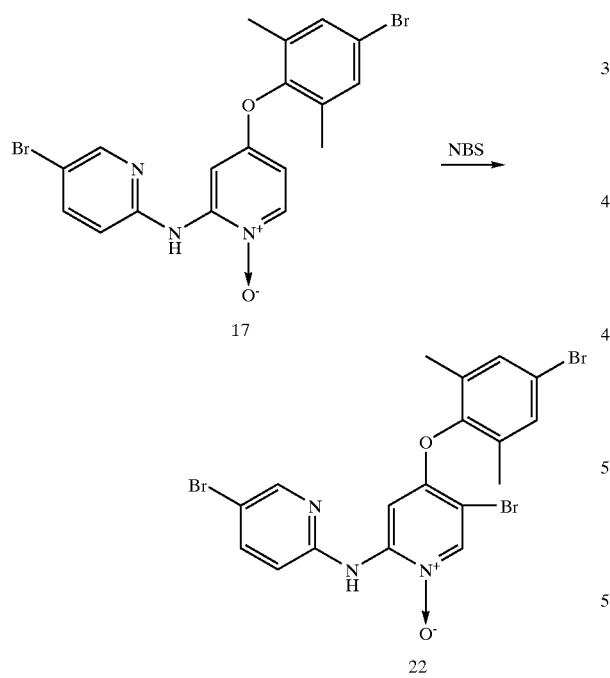

Synthesis of [5-Bromo-4-(4-bromo-2,6-dimethyl-phenoxy)-1-oxy-pyridin-2-yl]-(5-bromo-pyridin-2-yl)-amine (22): A solution of 17 (55mg, 0.12 mmol) in CH$_3$CN (2 mL) was treated with NBS (25 mg, 0.14 mmol, 1.2 equiv) and stirred overnight at room temperature. An additional 0.5 equiv of NBS (11 mg, 0.6 mmol) was added and the reaction was stirred for 48 h. The suspension was filtered and the solid washed to afford the desired product as a brown solid (21 mg, 33%) mp 230–234° C. $^1$H NMR (300 MHz, CDCl$_3$) δ9.57 (br s, NH), 8.44 (s, 1 H), 8.01 (d, J=2.2 Hz, 1 H), 7.97 (s, 1H), 7.68 (dd, J=2.2, 8.8 Hz, 1H), 7.34 (s, 2H), 6.80 (d, J=8.8 Hz, 1H), 2.15 (s, 6H).

Example 5

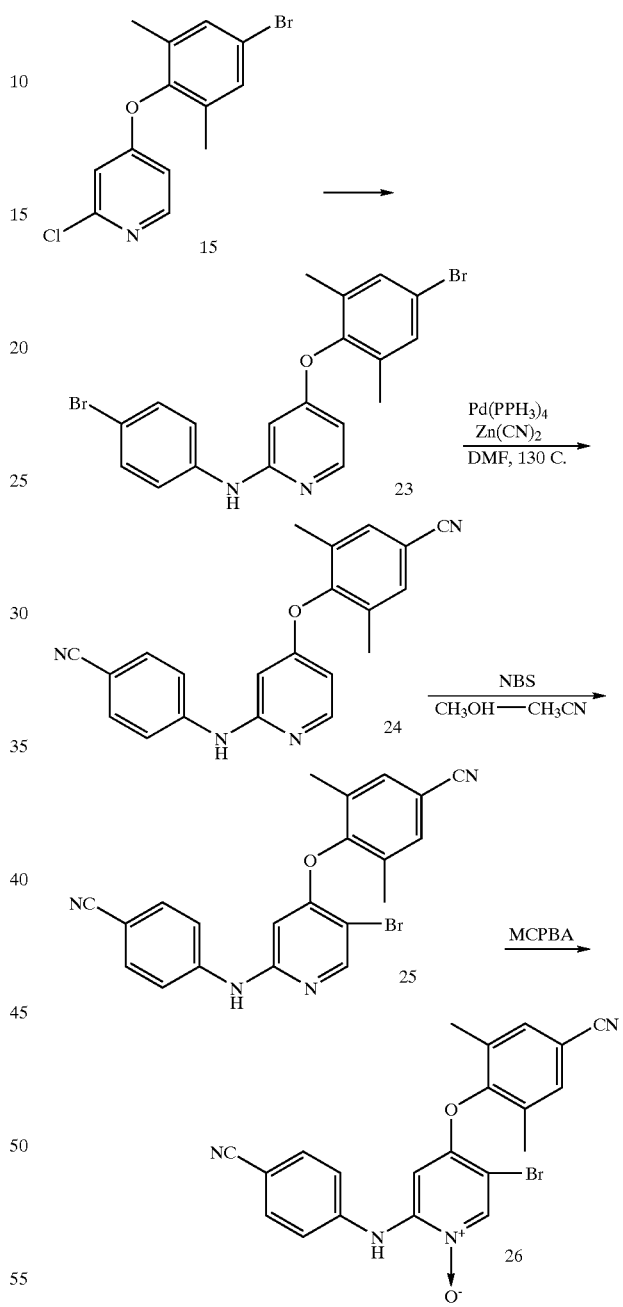

Synthesis of [5-Bromo-4-(4-Cyano-2,6-dimethyl-phenoxy)-1-oxy-pyridin-2-yl]-(4-cyano-phenyl)-amine (26)

Step A: [4-(4-Bromo-2,6-dimethyl-phenoxy)-pyridin-2-yl]-(4-bromo-phenyl)-amine (23): In a flask outfitted with a reflux condensor, 15 (1 g, 3.2 mmol) and 4-bromoaniline (1.1 g, 6.4 mmol, 2 equiv) were melted together at 190° C. for 5 h. The reaction was cooled to room temperature and the resulting black solid was dissolved in 4:1 THF-1N NaOH soln (5 mL) stirring overnight. The reaction was diluted with EtOAc and the organic phase was washed with 1 N NaOH soln, 0.1 M HCl soln. Activated charcoal was added and the organic phase was stirred at room temperature for 0.5 h, filtered through celite and concentrated. The resulting brown solid was recrystallized from $CH_2Cl_2$ (~4 mL) to provide the purified product as a white solid (1.2 g, 86%). $^1H$ NMR (300 MHz, $CDCl_3$) δ8.03 (d, J=5.9 Hz, 1H), 7.39 (d, J=8.8 Hz, 2H), 7.23 (m, 3H), 6.42 (s, NH), 6.19 (m, 2H), 6.14 (d, J=1.9 Hz, 1H), 2.10 (s, 6H).

Step B: [4-(4-Cyano-2,6-dimethyl-phenoxy)-pyridin-2-yl]-(4-cyano-phenyl)-amine (24): A mixture of 23 (1.1 g, 2.68 mmol), $Zn(CN)_2$ (407 mg, 3.48mmol, 1.3 equiv) and tetrakistriphenylphosphine palladium (0) (275 mg, 0.238 mmol, 0.09 equiv) in DMF (22 mL) was thoroughly degassed under high vacuum and heated to 130° C. for 7.5 h. The reaction mixture was partitioned between EtOAc and $H_2O$, extracted with EtOAc and the solid materials were removed by filtration through celite. The combined organics were washed with brine and concentrated. The resulting brown solid was triturated with hot $CH_2Cl_2$ to provide the desired product (632 mg). The filtrate was concentrated and purified by column chromatography ($SiO_2$, 25% EtOAc-hexane) to provide an additional 162 mg of product (794 mg total, 87%). $^1H$ NMR (300 MHz, $CDCl_3$) δ8.14 (d, J=5.8 Hz, 1H), 7.56 (d, J=1.8 Hz, 4 H), 7.45 (s, 2H), 6.64 (s, NH), 6.30 (dd, J=1.8, 5.8 Hz, 1H), 6.15 (m, 1H), 2.17 (s, 6H).

Step C: [5-Bromo-4-(4-Cyano-2,6-dimethyl-phenoxy)-pyridin-2-yl]-(4-cyano-ph nyl)-amine (25): A suspension of 24 (160 mg, 0.47 mmol) in $CH_3CN$—$CH_3OH$ (10:1, 11 mL) at 0° C. was treated with NBS (84 mg, 0.47 mmol, 1 equiv). After 30 min, the reaction was homogeneous and complete by TLC. Additional 24 (620 mg, 1.8 mmol), $CH_3CN$ (2 mL) and NBS (325 mg, 1.8 mmol, 1 equiv) were added and after 15 min, a precipitate had formed. The reaction was stirred at 0° C. for 90 min and the precipitate was collected and washed with $CH_3CN$ to provide 25 as a white solid (893 mg, 93%). $^1H$ NMR (300 MHz, $CDCl_3$) δ8.37 (s, 1H), 7.53 (s, 4H), 7.47 (s, 2H), 6.58 (s, NH), 5.68 (s, 1H), 2.21 (s, 6H).

Step D: [5-Bromo-4-(4-Cyano-2,6-dimethyl-phenoxy)-1-oxy-pyridin-2-yl]-(4-cyano-phenyl)-amine (26): A suspension of 25 (870 mg, 2.08 mmol) in $CH_2Cl_2$ (10 mL) was treated with MCPBA (68.7%, 657 mg, 3.8 mmol, 1.8 equiv) was stirred overnight. The reaction was filtered and washed with CH2C12 to remove the MCBA and the mother liquor, now a suspension was diluted with EtOAc (20–30 mL). Dimethyl sulfide was added and the reaction was stirred for 30 min. 1N NaOH soln (20 mL) was added and the reaction mixture was stirred for 2 h before filtering. The resulting solid was washed with CH2C12 (2x), 1N NaOH soln (5x), H2O (2x) CH2Cl2 (5x) and dried at 70° C. to provide the desired product as a pale yellow solid (570 mg, 69%). mp 254–256° C. $^1H$ NMR (300 MHz, $CDCl_3$) δ9.05 (br s, NH), 8.49 (s, 1H), 7.56 (d, J=8.8 Hz, 2H), 7.49 (s, 2H), 7.01 (d, J=8.8 Hz, 2H), 6.14 (s, 1H), 2.21 (s, 6H).

Utility

The compounds of this invention possess reverse transcriptase inhibitory activity and HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and in vitro RNA Transcripts

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at -70° C. The concentration of RNA was determined from the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin -CCCT-ATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 μM stocks in 2×SSC (0.3 M NaCl, 0.03 M sodium citrate), 0.05 M Tris pH 8.8, 1 mg/mL BSA. The biotinylated capture probes were prepared as 100 µM stocks in water.

Streptavidin Coated Plates

Streptavidin coated plates were obtained from DuPont Biotechnology Systems (Boston, Mass.).

Cells and Virus Stocks

MT-2 and MT-4 cells were maintained in RPMI 1640 supplemented with 5% fetal calf serum (FCS) for MT-2 cells or 10% FCS for MT-4 cells, 2 mM L-glutamine and 50 µg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were $1-3 \times 10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at $5 \times 10^5$ cells/mL in RPMI 1640, 5% FCS for bulk infections or at $2 \times 10^6$/mL in Dulbecco's modified Eagles medium with 5% FCS for infection in microtiter plates. Virus was added and culture continued for 3 days at 37° C.

HIV RNA Assay

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline (PBS), 0.05% Tween 20) A second hybridization of reporter probe to the immobilized complex of capture probe and hybridized target RNA was carried out in the washed streptavidin coated well by addition of 120 µl of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer (2.5 M diethanolamine pH 8.9 (JBL Scientific), 10 mM MgCl2, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5 \times 10^5$ per mL ($1 \times 10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 µg/mL. $IC_{90}$ values of other antiviral compounds, both more and less potent than ddC, were reproducible using several stocks of HIV-1 (RF) when this procedure was followed. This concentration of virus corresponded to $\sim 3 \times 10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of PDAB 72 in vitro RNA transcript. The $IC_{90}$ for ddC, determined in each assay run, should be between 0.1 and 0.3 µg/mL. Finally, the plateau level of viral RNA produced by an effective reverse transcriptase inhibitor should be less than 10% of the level achieved in an uninhibited infection. A compound was considered active if its $IC_{90}$ was found to be less than 20 µM.

For antiviral potency tests, all manipulations in microtiter plates, following the initial addition of 2X concentrated compound solution to a single row of wells, were performed using a Perkin Elmer/Cetus ProPette.

Compounds tested in the assay described below are considered to be active if they exhibit a $EC_{50}$ of $\leq 10$ µM. Compounds of the present invention have $EC_{50}$'s of $\leq 10$ µM, $EC_{50}$'s of $\leq 0.01$ µM or have $EC_{50}$'s of $\leq 0.001$ µM.

Using the methodologies described below, a number of compounds of the present invention were found to exhibit a $EC_{50}$ of $\leq 10$ µM, thereby confirming the utility of the compounds of the present invention as effective HIV reverse transcriptase inhibitors.

Reverse Transcriptase (RT) Assay Cells and Virus Stocks

MT-2 cells were maintained in RPMI 1640 supplemented with 10% fetal calf serum (FCS) and 2 mM L-glutamine. All the reagents were purchased from Gibco BRL, MD. HIV-1 IIIB, HXB2, NL4-3 and 16 drug-resistant mutant strains (IIIB-K103N/L100I, IIIB-K103N/Y181C, NL-K103N, NL-Y188L, NL-K101E, NL-K103N/K101E, HXB2-K101P, HXB2-K101Q, HXB2-G190S, HXB2-K103N/K101Q, HXB2-K103N/V108I, HXB2-K103N/G190A, HXB2-K103N/P225H, HXB2-Yl8lC/G190A, HXB2-K103N/Y181C/G190S and HXB2-K103N/V108I/P225H) were propagated in MT-2 cells. Virus stocks were harvested approximately 7 days after acute infection of MT-2 cells and stored as aliquots in liquid nitrogen. The infectious titers of the HIV-1 stocks ranged from 0.025 to $29.1 \times 10^5$ $TCID_{50}$ (50% tissue culture infectious dose/mL) as measured by an infectivity assay (virus yield Assay) (Johnson V A, Byington R T. 1990 Infectivity assay [virus yield assay], p. 71–76. In Aldovini A and Walker BD [ed.] Techniques in HIV Research, Stockton Press, N.Y.). Each aliquot of virus stock used for infection was thawed only once.

For evaluation of antiviral efficacy, MT-2 cells to be infected were subcultured one day prior to infection. On the day of infection, MT-2 cells were infected with HIV-1 viruses at an MOI (multiplicity of infection) of 0.002 and resuspended at $1 \times 10^5$ cells/mL in RPMI 1640 with 10% FCS in microtiter plates. The infected MT-2 cells were maintained in culture in the presence or absence of serially diluted compounds for 5 days at 37° C. in a humidified 5% $CO_2$ incubator.

RT Assay

Both polyadenylic acid (poly A) and oligo dT ($pdT_{12-18}$) were purchased from Amersham Pharmacia Biotech, N.J. 5'[$^3$H]-thymidine triphosphate ([$^3$H]-TTP) was obtained from NEN Dupont, Mass.

An RT assay (Barbara J. Potts. 1990 "MINI" reverse transcriptase [RT] assay, p. 103–106. In Aldovini A and Walker BD [ed.] Techniques in HIV Research, Stockton Press, N.Y.) was used to monitor the virus yield. For the RT assay, 40 μl of cocktail (62.5 mM Tris [pH 7.8 ], 6.25 μg/ml poly A, 1.97 μg/ml oligo dT, 6.19 mM $MgCl_2$, 93.8 mM KCl, 0.063% NP-40, 2.5 mM dithiothreitol [DTT], 1 μCi of [$^3$H]-TTP) was mixed with 20 μl of culture supernatant per well in a 96-well plate. The plate was incubated at 37° C. for one hour and 10 μl of sample from each well was loaded on a DEAE fillermat (Wallac, Md.). The membrane was washed four times in 2×SSC (0.3 M NaCl and 0.03M Trisodium Citrate) and two times in 95% ethanol. After air dry, the membrane was sealed in a bag with 5 ml Beta-Scint fluid and read using a Wallac Trilux.

Calculation of 50% Effective Concentration ($EC_{50}$)

The 50% effective concentration ($EC_{50}$) represents the concentration of a compound that decreases the RT activity to 50% of that produced from the untreated control wells. The $EC_{50}$ was calculated using the exponential form of the median effect equation where $(Fa)=1/[1+(ED_{50}/drug\ conc.)^m]$ (Johnson VA, Byington RT. 1990 Infectivity assay [virus yield assay], p. 71–76. In Aldovini A and Walker BD [ed.] Techniques in HIV Research, Stockton Press, N.Y.).

XTT Assay

Cells and Virus Stocks

The cell maintenance and virus propagation are the same as described for the RT assay.

For evaluation of antiviral efficacy (host cell protection), MT-2 cells were infected with HIV-1 viruses at an MOI of 0.002 and resuspended at $1 \times 10^5$ cells/mL in RPMI 1640 (without phenol red) plus 10% FCS and then dispensed into 96 well microtiter plates. The infected MT-2 cells were cultured in the presence of serially diluted compounds for 5 days at 5% $CO_2$ and 37° C. Uninfected MT-2 cells were also cultured in each plate as a control.

XTT Assay

XTT can be reduced by the mitochondria reductase in living cells to produce colored XTT formazan (Weislow, O. S., R. Kiser, D. L. Fine, J. Bader, R. H. Shoemaker, and M. R. Boyd. 1989. New soluble-formazan assay for HIV-1 cytopathic effects: application to high-flux screening of synthetic and natural products for AIDS-antiviral activity. Journal of National Cancer Institute 81:577–586.). XTT (2,3-bis[2-methoxy-4-nitro-5-sulfophenyl]-5-[(phenylamino)carbonyl]-2H-tetrazolium hydroxide) and PMS (phenazine methosulfate) were purchased from Sigma, Mo. XTT was dissolved at 1 mg/ml in warmed RPMI 1640 (without phenol red and FCS) and PMS was added to a final concentration of 0.025 mM. This solution was dispensed into plates at 50 μl/well. The plates were incubated in the dark at 37° C. for 4 hours and the O.D. was read at a wavelength of 450 nm using a spectromax.

Calculation of 50% Effective Concentration ($EC_{50}$)

Since T-tropic HIV-1 strains such as IIIB, HXB2 and NL4-3 can kill the host cells, effective compounds are able to inhibit the virus replication and protect the host cells from virus—induced cell killing. The $EC_{50}$ is the concentration of a compound that increases cell viability of the infected wells to 50% of that from the uninfected control cells. It was calculated using the same method as mentioned above.

MTS Assay

Cells and Virus Stocks

The cell maintenance and virus propagation are the same as mentioned in the RT assay and XTT assay sections.

MTS Assay

The principle of the MTS assay is similar to that of XTT assay mentioned above. The conversion of MTS into aqueous, soluble formazan is accomplished by dehydrogenase enzymes found in metabolically active cells. MTS [3-(4,5-dimethylthiazol-2-yl)-5-(3-carboxymethoxyphenyl)-2-(4-sulfophenyl)-2H-tetrazolium] was purchased from Promega, Wis.

MTS was prepared at a working concentration of 2 mg/ml in PBS and PMS added to reach 0.025 mM. The MTS/PMS mixture was distributed to testing plates at 40 μl/well. The plates were placed in 37° C. incubator for two to four hours and then read at 490 nm in a plate reader.

Calculation of 50% Effective Concentration ($EC_{50}$)

It was similar to that for XTT assay as mentioned above.

Cytotoxicity Assay

Cells and Virus Stocks

The cell maintenance and virus propagation are the same as mentioned in the RT assay and XTT assay sections.

Cytotoxicity

MT-2 cells were cultured in the presence of serially-diluted inhibitors for 6 days and cell viability was quantitated using an XTT/MTS assay to calculate the $CC_{50}$ values. The $CC_5O$ is the concentration of a compound that decreases cell viability of the treated wells to 50% of that from the untreated control cells. It was calculated using the same method as mentioned in the RT assay and XTT assay sections.

Protein Binding and Mutant Resistance

In order to characterize NNRTI compounds for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.
2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

The protein binding for the compound was also measured in an assay designed to solely measure protein binding. The in vitro protein binding of the compound of the present invention was determined by equilibrium dialysis using pooled human serum. The compound as added to human serum to achieve a final concentration of 10 $\mu$M. An aliquot of the spiked serum was then loaded to one side of an assembled equilibrium dialysis teflon cell, while potassium phosphate buffer (0.133M, pH 7.4) was loaded to the other side of the cell. After incubation at 37° C. , the serum and buffer samples were collected, extracted and the compound concentrations determined by liquid chromatography mass spectral analysis. The percent of drug unbound was calculated by dividing the buffer concentration by the serum concentration and then multiplying by 100.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A capsule formulation of the present invention can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A soft gelatin capsule formulation of the present invention can be prepared as follows. A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A tablet formulation of the present invention can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension formulation can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral formulation suitable for administration by injection can be prepared by stirring 1.5% by weight of active ingredient in 10% by volume propylene glycol and water. The solution is sterilized by commonly used techniques.

Combination Administration of Therapeutic Agents

The present invention provides a method for the treatment of HIV infection which comprises administering, in combination, to a host in need thereof a therapeutically effective amount of the following:

(a) a compound of formula (I); and (b) at least one compound selected from the group consisting of HIV reverse transcriptase inhibitors and HIV protease inhibitors, in one or more sterile containers.

Each therapeutic agent component of this combination method (i.e., component (a) and (b) set forth above) can independently be administered in any separate dosage form, such as those described above, and can be administered in various ways, as described above. In the following description component (b) is to be understood to represent one or more agents as described previously. Each individual therapeutic agent comprising component (b) may also be independently be administered in any separate dosage form, such as those described above, and can be administered in various ways, as described above.

Components (a) and any one or more of the agents comprising component (b) of the combination method of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes or dosage forms (for example, one component of the combination method may be administered orally, and another component may be administered intravenously).

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the combination method of this invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b) may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment HIV infection (as defined previously). In another embodiment, the package insert states that the pharmaceutical composition can be used in combination (as defined previously) with a second therapeutic agent to treat HIV infection. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc., that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

As will be appreciated by one of skill in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

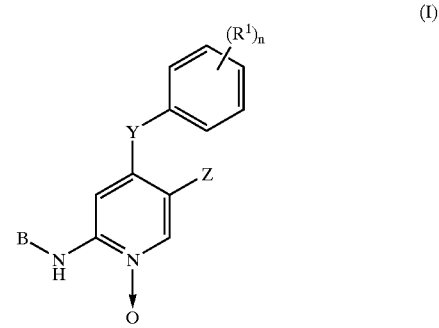

or a stereoisomeric form or mixture of stereoisomeric forms or a pharmaceutically acceptable salt form thereof, wherein B is selected from phenyl substituted with 1–3 X, and a 5–6 membered heterocyclic system containing 1–4 heteroatoms selected from N, O, and S, substituted with 1–3 X;

$R^1$, at each occurrence, is individually selected from F, Cl, Br, I, CN, and $C_{1-4}$ alkyl, $C_{1-3}$ alkoxy;

n is selected from 1, 2, 3 and 4;

X is selected from CN, F, Cl, Br, and I;

Y is selected from —$CH_2$—, —NH—, and —O—; and

Z is selected from F, Cl, Br, CN, and $C_{1-4}$ alkyl.

2. A compound of claim 1, wherein the compound is of formula (I-i):

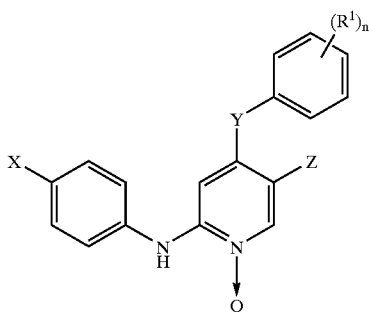

or a stereoisomeric form or mixture of stereoisomeric forms or a pharmaceutically acceptable salt form thereof, wherein $R^1$, at each occurrence, is individually selected from F, Cl, Br, I, CN, and $C_{1-4}$ alkyl, $C_{1-3}$ alkoxy;

n is selected from 1, 2, 3 and 4;

X is selected from CN, F, Cl, Br, and I;

Y is selected from —$CH_2$—, —NH—, and —O—; and

Z is selected from F, Cl, Br, CN, and $C_{1-4}$ alkyl.

3. The compound of claim 1, wherein the compound is of formula (I-ii)

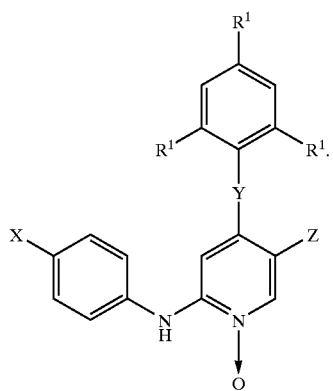

4. The compound of claim 1, wherein $R^1$, at each occurrence, is individually selected from CN, F, Cl, Br, methyl, ethyl, and propyl, i-propyl, methoxy, ethoxy, propoxy, i-propxoy.

5. The compound of claim 1, wherein

X is selected from F, Cl, Br, and CN.

6. The compound of claim 1, wherein

Z is selected from Z is selected from Cl, Br, CN, methyl, ethyl and propyl.

7. The compound of claim 1, wherein

Y is —$CH_2$—.

8. The compound of claim 1, wherein

Y is —NH—.

9. The compound of claim 1, wherein

Y is —O—.

10. The compound of claim 1, wherein

B is selected from phenyl substituted with 1–3 X, and a 5–6 membered heterocyclic system containing 1–4 heteroatoms selected from N, O, and S, substituted with 1–3 X, wherein the heterocyclic system is selected from pyridine, pyrimidine, and thiazole.

11. The compound of claim 2, wherein

X is selected from F, Cl, Br, and CN.

12. The compound of claim 2, wherein

Z is selected from Z is selected from Cl, Br, CN, methyl, ethyl and propyl.

13. The compound of claim 2, wherein

Y is —$CH_2$—.

14. The compound of claim 2, wherein

Y is —NH—.

15. The compound of claim 2, wherein

Y is —O—.

16. The compound of claim 2, wherein

B is selected from phenyl substituted with 1–3 X, and a 5–6 membered heterocyclic system containing 1–4 heteroatoms selected from N, O, and S, substituted with 1–3 X, wherein the heterocyclic system is selected from pyridine, pyrimidine, and thiazole.

17. The compound of claim 1, wherein the compound is selected from:

5-bromo-2-(4-chloroanilino)-4-(2,4,6-trimethylphenoxy) pyridine-N-oxide;

5-bromo-2-(4-chloroanilino)-4-(2,4,6-trimethylanilino) pyridine-N-oxide;

6-[5-Bromo-4-(4-cyano-2,6-dimethyl-phenoxy)-1-oxy-pyridin-2-ylamino]-nicotinonitrile;

[5-Bromo-4-(4-bromo-2,6-dimethyl-phenoxy)-1-oxy-pyridin-2-yl]-(5-bromo-pyridin-2-yl)-amine; and

[5-Bromo-4-(4-Cyano-2,6-dimethyl-phenoxy)-1-oxy-pyridin-2-yl]-(4-cyano-phenyl)-amine.

18. A pharmaceutical composition comprising a pharmaceutically acceptable carrier and a therapeutically effective amount of a compound according to one of claim 1 or pharmaceutically acceptable salt form thereof.

19. A method for treating HIV infection which comprises administering to a host in need of such treatment a therapeutically effective amount of a compound according to one of claim 1 or pharmaceutically acceptable salt form thereof.

20. A method of treating HIV infection which comprises administering, in combination, to a host in need thereof a therapeutically effective amount of:

(a) a compound according to one of claim 1; and, (b) at least one compound selected from the group consisting of HIV reverse transcriptase inhibitors, HIV protease inhibitors, fusion inhibitors, and CCR-5 inhibitors.

21. A method of claim 20, wherein the reverse transcriptase inhibitor is selected from the group AZT, ddC, ddI, d4T, 3TC, delavirdine, efavirenz, nevirapine, trovirdine, MKC-442, HBY 097, HBY1293, GW867, ACT, UC-781, UC-782, RD4-2025, MEN 10979, AG1549 (S1153), TMC-120, TMC-125, Calanolide A, and PMPA, and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, ABT-378, DMP-450, AG-1776, VX-175, MK-944, and VX-478, the CCR-5 inhibitor is selected from TAK-779 (Takeda), SC-351125 (SCH-C, Schering) and SCH-D (Schering), and the fusion inhibitor is selected from T-20 and T1249.

22. A method of claim 21, wherein the reverse transcriptase inhibitor is selected from the group AZT, efavirenz, and 3TC and the protease inhibitor is selected from the group saquinavir, ritonavir, nelfinavir, and indinavir.

23. A method of claim 22, wherein the reverse transcriptase inhibitor is AZT.

24. A method of claim 23, wherein the protease inhibitor is indinavir.

25. A pharmaceutical kit useful for the treatment of HIV infection, which comprises a therapeutically effective amount of:
(a) a compound according to one of claim 1; and,
(b) at least one compound selected from the group consisting of HIV reverse transcriptase inhibitors and HIV protease inhibitors, in one or more sterile containers.

* * * * *